US00PP26061P3

(12) United States Plant Patent
Bodapati et al.

(10) Patent No.: US PP26,061 P3
(45) Date of Patent: Nov. 10, 2015

(54) ***PONGAMIA* TREE NAMED 'K606'**

(50) Latin Name: ***Pongamia pinnata* (L) Pierre**
Varietal Denomination: K606

(71) Applicant: TERVIVA BIOENERGY, Oakland, CA (US)

(72) Inventors: Naidu Bodapati, Oakland, CA (US); Marshall Mackay, Oakland, CA (US)

(73) Assignee: Terviva Bioenergy, Oakland, CA (US)

( * ) Notice: Subject to any disclaimer, the term of this patent is extended or adjusted under 35 U.S.C. 154(b) by 71 days.

(21) Appl. No.: 13/987,127

(22) Filed: Jul. 1, 2013

(65) Prior Publication Data

US 2015/0020252 P1 Jan. 15, 2015

(51) Int. Cl.
*A01H 5/00* (2006.01)

(52) U.S. Cl.
USPC ..... Plt./216

(58) Field of Classification Search
USPC ..... Plt./216
CPC ..... A01H 5/00
See application file for complete search history.

(56) References Cited

PUBLICATIONS

U.S. Appl. No. 13/987,125, filed Jul. 1, 2013, Bodapati et al.
U.S. Appl. No. 13/987,126, filed Jul. 1, 2013, Bodapati et al.

*Primary Examiner* — Kent L Bell
(74) *Attorney, Agent, or Firm* — Dentons US LLP

(57) ABSTRACT

'K606' is a new *Pongamia* tree distinguished by having a deep-green, dense crown, high-angle branches, typically unbranched inflorescences, short mature rachises, consistent and abundant production of seed pods, and high oil content of the seeds.

5 Drawing Sheets

Latin name of the genus and species of the plant claimed: *Pongamia pinnata* (L) Pierre.

Cultivar denomination: 'K606'.

BACKGROUND OF THE INVENTION

The invention relates to a new and distinct cultivar of *Pongamia* tree (*Pongamia pinnata* (L) Pierre) named 'K606'. 'K606' was discovered by the inventors growing in an urban cultivated area in southeastern Queensland, Australia, wherein it and neighboring trees are grown for shade and other landscape amenities. The parentage of this tree is unknown, as is typical for trees cultivated in landscape plantings of this type.

'K606' has been reproduced asexually through vegetative cuttings.

'K606' has not been made publicly available more than one year prior to the filing date of this application.

SUMMARY OF THE INVENTION

A new and distinct variety of *Pongamia* tree (*Pongamia pinnata* (L) Pierre) named 'K606', characterized by a deep-green, dense crown, high-angle branches, and typically unbranched inflorescences, with mature rachises tending to be shorter than average. Flowering and fruit set occur annually, or nearly so. Oil-rich seeds contain 38.6% oil on a dry-weight basis. The tree is vigorous and reasonably resistant to disease pests.

The original tree (and source of clonal material) was identified and selected primarily on the basis of its consistent and abundant production of seed pods, coupled with the high oil content (38.6%, dry-weight basis) of its seeds. This selected individual was assigned identity number 'K606'. Subsequently, branch cuttings were collected from the donor tree and rooted by treating the cuttings with rooting hormone indolebutyric acid (IBA) using either an aqueous solution of IBA (500 ppm) or a commercially available rooting powder. Dehydration of the cuttings was avoided by placing them in moistened rooting medium within a humid enclosed chamber. Rooting success varies from one collection event to another, which is normal for cuttings from mature trees. Typically 10% or more of the cuttings initiated root development within 3 to 4 weeks. Cuttings were rooted in Brisbane, Australia as well as in Texas, U.S.A. These asexually propagated rooted cuttings remain true-to-type, and show considerable resemblance among one another, after accounting for differences for variation in overall size of the cuttings from which the individual trees were derived.

Similar to *Pongamia* cultivars 'K128b' (U.S. Patent Publ. No. 2015/0020250) and 'K140' (U.S. Patent Publ. No. 2015/0020251), 'K606' has a strong tendency to produce regular crops of pods each year. Seed oil content, at 38.6%, is similar to that of 'K128b' (38.5%), but is substantially less than that of 'K140'. Branches in the crown of 'K606' tend to be oriented more vertically (upright) than branches in the spreading crowns of 'K128b' and 'K140'. This tendency is also apparent in asexually propagated plants. Inflorescences borne on 'K606' generally contain fewer florets (16 to 41, averaging 33) than cultivars 'K128b' and 'K140'. Leaves on 'K606' usually contain 5 leaflets, rarely 7. This contrasts with cultivars 'K128b' and 'K140', in which leaves with 7 leaflets are relatively common.

BRIEF DESCRIPTION OF THE DRAWINGS

This new *Pongamia* tree is illustrated by the accompanying photographs, which show the tree's form, branches, foliage, leaves, trunk, pods, and seeds. The colors shown are as true as can be reasonably obtained by conventional photographic procedures.

DETAILED BOTANICAL DESCRIPTION

Figure 1:
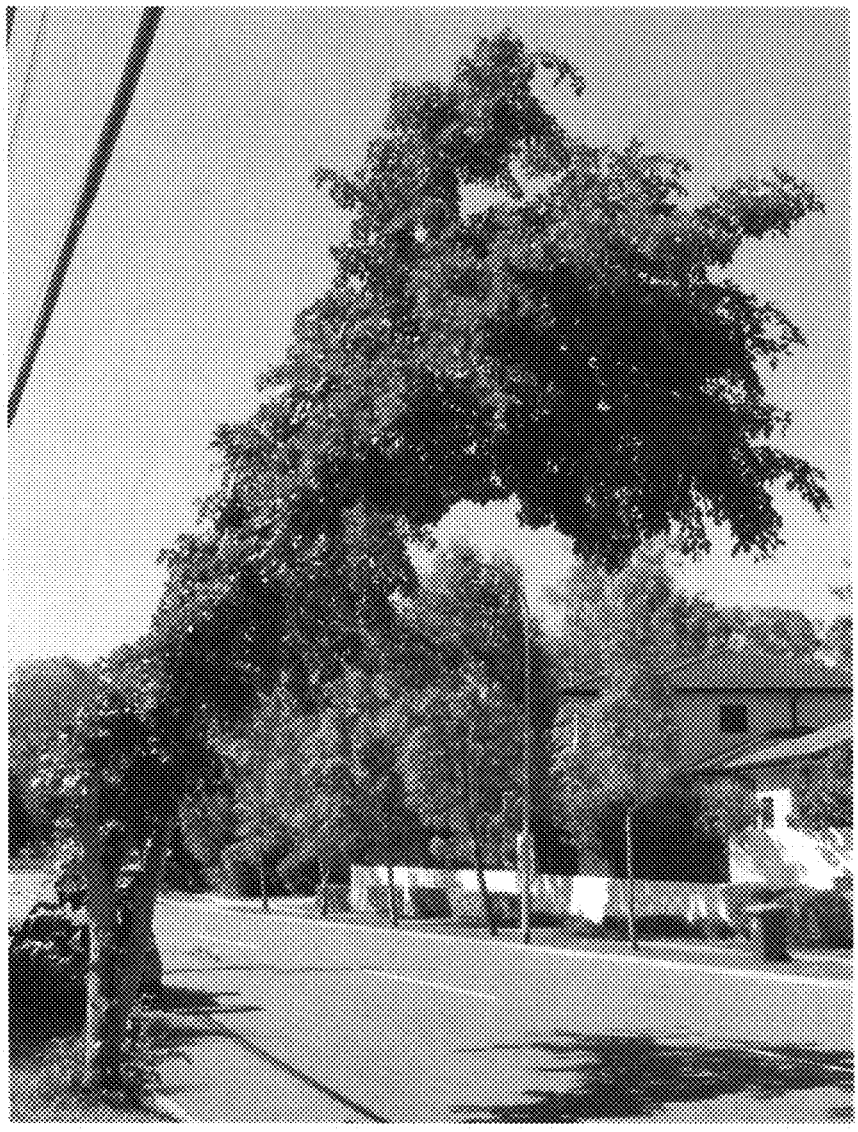
FIG. 1—shows an overview of 'K606' as seen from the street. The crown has been heavily pruned to maintain clearance from overhead utility lines and from street traffic.
Figure 2:
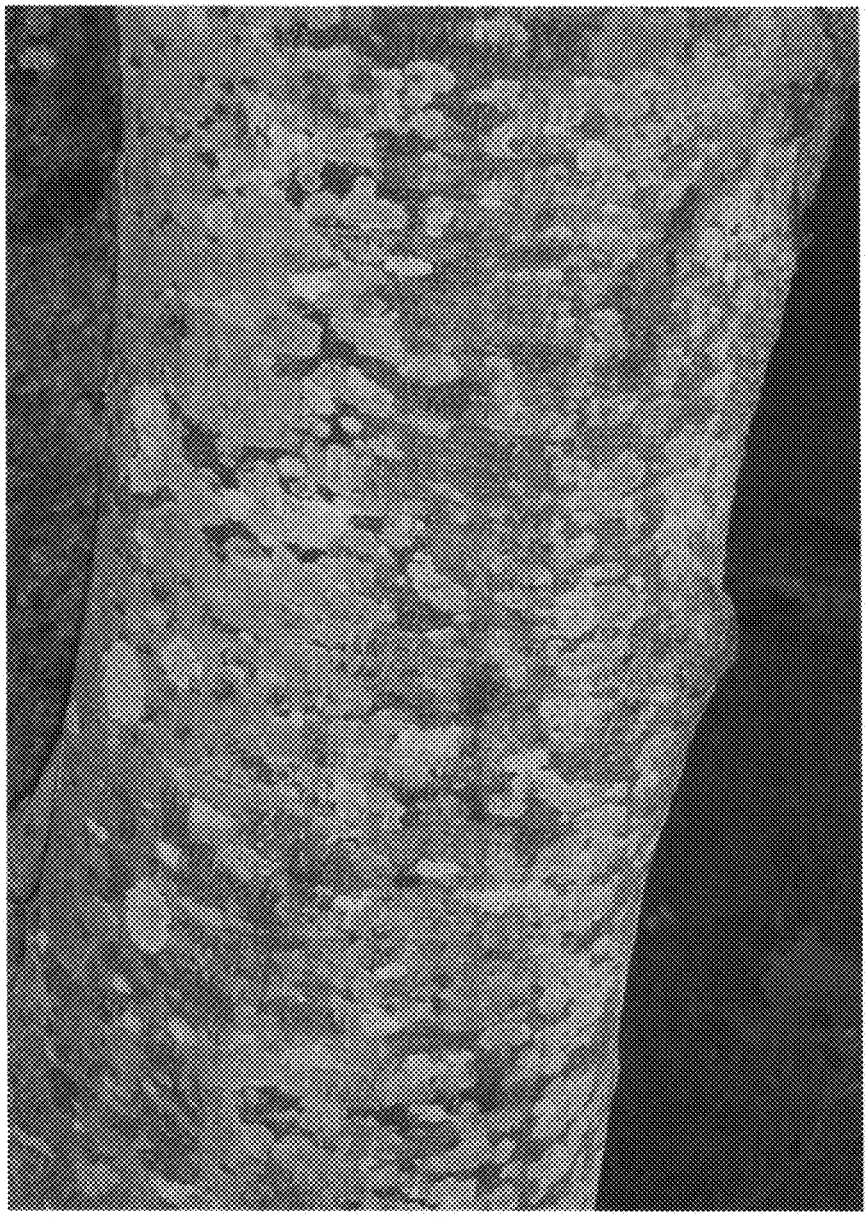
FIG. 2—shows the smooth gray bark on the main trunk. Mottled patches of lighter and darker gray primarily reflect differences in lichen growth. Stretched lenticular scars appear as horizontal striations along the bark.
Figure 3:
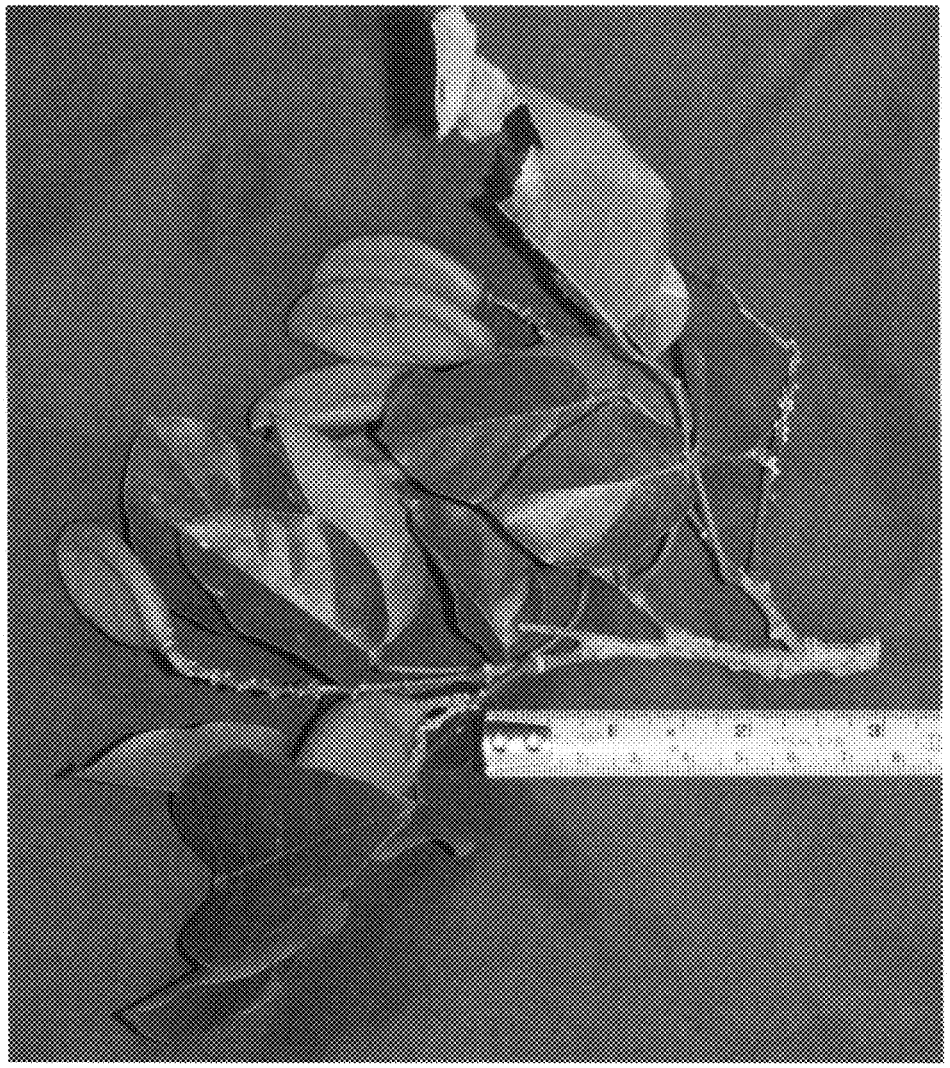
FIG. 3—shows lateral shoots (short shoots) bearing both leaves and immature seed pods.
Figure 4:
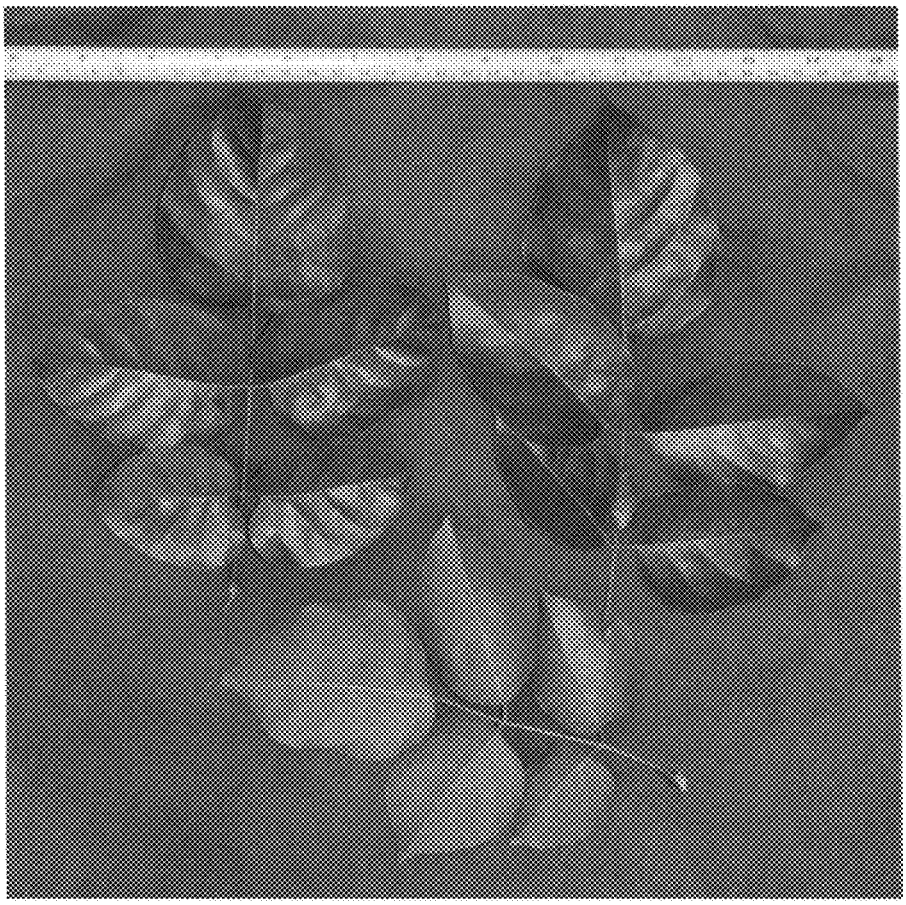
FIG. 4—shows pinnately compound leaves with typically 5 leaflets. Leaflets are ovate to cordate in shape with a cuspidate to mucronate apex. Leaflet venation tends to be arcuate. The adaxial leaf surface is a shiny deep green, whereas the abaxial surface (underside) is a lighter green and not shiny (lower leaf).
Figure 5:
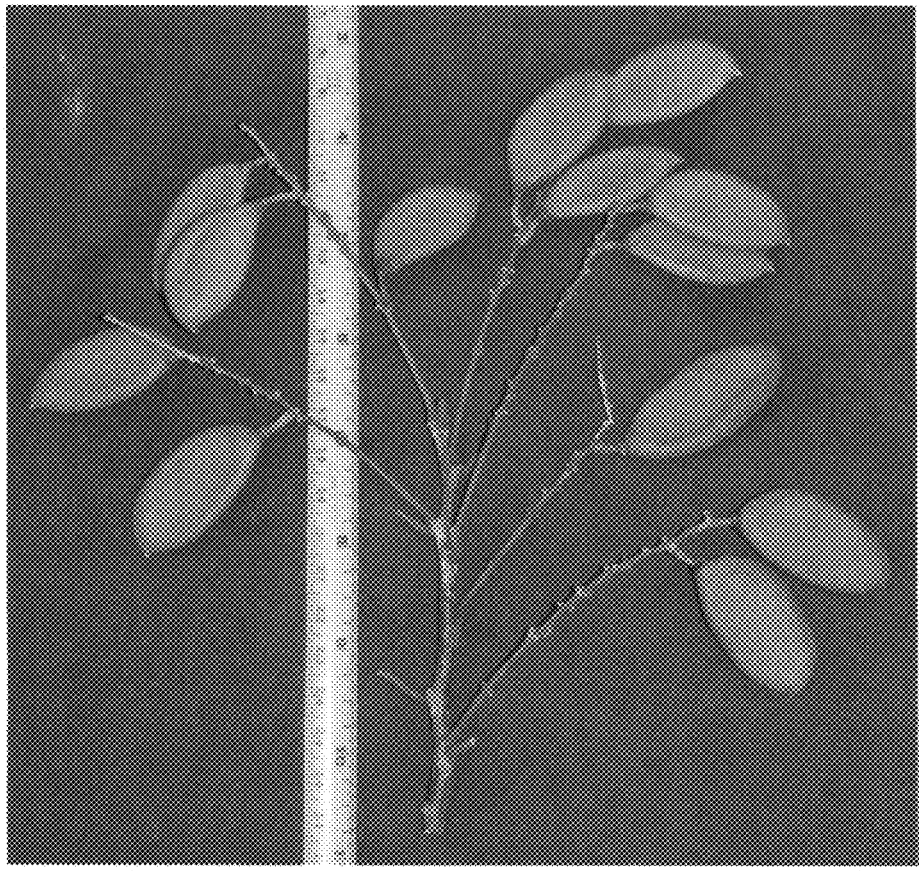
FIG. 5—shows unbranched fruit clusters showing immature pods attached to their respective central rachis. Leaves have been removed for visibility. The branch shown has 6 rachis borne in the axils of basal leaves. Each rachis bears 1 to 4 immature pods.

The following detailed description sets forth the distinctive characteristics of 'K606'. Hereafter, standardized color codes refer to The Royal Horticultural Society (R.H.S.) Mini Colour Chart.

Classification:

*Family*.—Fabaceae.

*Botanical*.—*Pongamia pinnata* (L) Pierre; also called *Millettia pinnata* (L) Panigrahi, *Derris indica* (Lam.) Bennet, *Pongamia glabra* Vent, and *Cytisus pinnatus* (L).

*Common name*.—Pongam tree, or pongam oiltree.

*Cultivar name*.—'K606'.

Plant description:

Tree:

*Size*.—Modestly vigorous tree of reasonable size and stature, 10 m in height. The narrow crown has been heavily pruned to avoid overhead utility lines and to minimize interference with street traffic. The dripline is roughly 7 m×7 m, but this varies from year to year depending on crown pruning.

*Trunk*.—The main stem is bifurcated at a height of 80 cm from the ground, and subsequently branches several more times shortly above. Breast-height diameters of the two major stems are 22 and 17 cm. The trunk has numerous epicormic branches at its base, many of which have been removed by pruning. The length of one flush on an epicormic shoot ranges from 19 to 70 cm long and from about 4.0 to 7.45 mm in diameter.

*Bark*.—Smooth, grey, with some mottling, and many lighter grey flecks, likely caused by lichen growth. The trunk bears numerous horizontal striations which appear to have resulted from stretched lenticular scars.

*Form*.—Decurrent crown, artificially pruned into a narrow form. Outer branches are somewhat downward arching.

Branches: The lowest two branches (a bifurcated trunk) are noticeably forked. Above this, the lower (and larger) branches adjoin the main stem with similarly high branch angle (less than 45° between trunk and branch). The color of these branches closely resembles the color of the main stem. Branch length is not an informative characteristic of this tree due to regular pruning.

*Branching habit*.—Growth and size of lateral branches are considerably less than that of the main branches. Many smaller branches occur higher in the crown.

*Buds and shoots*.—Terminal buds are absent. Young shoots emerge from naked lateral buds, with the most distal bud giving rise to a terminal shoot. Buds are hemispherical and range from 3.0 to 5.0 mm wide at their base. Buds protrude outward 2.2 to 3.5 mm from the stem and are between 1.3 to 1.6 mm thick. The typical bud color is light olive (RHS 152B) and on younger material can be strong yellowish green (RHS 144A).

*Terminal shoots*.—The seasonal elongation of terminal shoots is modest, ranging from 9.2 to 13.3 cm (averaging 9.9 cm) and encompassing an average of 7 internodes. Stem diameters of terminal shoots range from 4.6 to 14.6 mm in diameter.

*Lateral shoots*.—Seasonal elongation of lateral shoots is even shorter than for terminal shoots, and can be as small as 3.1 cm with 3 internodes. Diameters of lateral shoots range from 3.5 to 4.4 mm (average 4.1 mm).

*Shoot and twig surfaces*.—Woody twigs have leaf scars that are 4.0 to 5.5 mm wide, showing traces of three vascular bundles. The central scar tends to have a border that is less distinct than the outer two. The youngest shoots are distinctly green and flexible, with no lenticels apparent to the naked eye. As shoots mature, their color shifts from green to tan and prominent lenticels become visible as raised, light-colored corky circles approximately 1.5 mm in diameter.

Leaves: Pinnately compound leaves bear typically 5 deep-green leaflets. Leaves are arranged alternately along the stem.

*Size and shape*.—The outline of a compound leaf is roughly oval to elliptic, with a length of 19.7 to 23.1 cm (average 21.3 cm) and a width of 15.7 to 19.6 cm (average 18.3 cm).

*Leaflets*.—Blades of individual leaflets are ovate to cordate in shape with a cuspidate to mucronate apex with an entire margin. Leaflet venation tends to be arcuate. Blades of terminal leaflets range in width from 7.7 to 8.6 cm (average 8.0 cm) and in length from 8.1 to 9.9 cm (average 9.3 cm). The smallest leaflet on a leaf tends to be a basal leaflet, ranging in width from 5.1 to 5.4 cm (average 5.3 cm) and in length from 5.3 to 7.1 cm (average 6.3 cm).

*Leaflet color, surface, and texture*.—Leaflets are glabrous on both abaxial and adaxial surfaces. Young leaves exhibit a strikingly glossy cuticle on their adaxial surface. The adaxial surface is deep yellowish green (RHS 141A), while the abaxial surface is moderate olive green (RHS 146A) and less glossy. Leaflets turn a darker shade of green (moderate olive green, RHS 137A) as they age and become increasingly sclerophyllous.

*Stipules*.—A pair of small stipules subtends the youngest leaves on a shoot. They remain for only a short duration before they dehisce.

Flowers and inflorescences: Hermaphroditic florets are borne on an indeterminate inflorescence.

*Inflorescence structure*.—Several florets are clustered into a fascicle node, which are more-or-less evenly distributed along a rachis. The entire inflorescence is a pseudoraceme. Most inflorescences are unbranched, but some are branched.

*Position in crown*.—Inflorescences most commonly occur on lateral shoots rather than on terminal shoots. From 1 to 6 axillary inflorescences may occur on a shoot, but more typically, only 2 to 3 are observed. Inflorescences are borne in the basal leaf axils of the current year's vegetative flush, near the distal end of the prior year's shoot growth. Each rachis may hold from 16 to 41 florets (averaging 33), which tends to be lower than average relative to other elite *Pongamia* trees.

*Florets*.—Emerge acropetally from an ovoid calyx. Zygomorphic florets consist of 5 pinkish-white petals: 2 keel, 2 wing, and a standard (or banner) petal.

*Flowering period*.—Relative to other *Pongamia* trees in the general area, 'K606' tends to flower about mid-range into the flowering period (from November to December in southeastern Queensland, Australia).

Fruits: Seed pods usually bear a single seed. An underdeveloped (and much smaller) seed is also observed in some pods.

*Shape and color*.—Developing fruits first appear as dark-green flattened pods, expanding in size into lighter green and eventually tan-colored woody pods.

*Crown distribution*.—Pods can occur throughout the crown, but are most prevalent towards the outer portions of the crown.

*Fruit clusters*.—Pods within a cluster are connected by the rachis of the inflorescence from which they developed.

*Dimensions*.—Fruits begin to ripen in late October (in southeastern Queensland, Australia), about 10 months after flowering.

Seeds: Typically borne singly in pods.

*Seed oil*.—Oil content is higher than average, at 38.6% oil on a dry-weight basis.

*Nut crop*.—Regular bearer.

*Crop frequency*.—Most *Pongamia* trees rarely produce abundant nut crops across multiple years, instead bearing fruit biennially or less frequently. 'K606' is unusual in that it bears fruit and seeds during most years.

*Ripening*.—Fruit ripening begins in late October and extends into December. If undisturbed, pods remain in the crown for several weeks after they ripen.

What is claimed is:

1. A new and distinct variety of *Pongamia pinnata* (L) Pierre tree called 'K606' as illustrated and described herein.

* * * * *